(12) United States Patent
Allegrini et al.

(10) Patent No.: US 9,079,831 B2
(45) Date of Patent: Jul. 14, 2015

(54) PROCESS FOR THE PREPARATION OF SULFONAMIDE COMPOUNDS

(71) Applicant: DIPHARMA FRANCIS S.r.l., Baranzate (MI) (IT)

(72) Inventors: Pietro Allegrini, Baranzate (IT); Simone Mantegazza, Baranzate (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 0 days.

(21) Appl. No.: 14/243,058

(22) Filed: Apr. 2, 2014

(65) Prior Publication Data

US 2014/0303402 A1 Oct. 9, 2014

(30) Foreign Application Priority Data

Apr. 9, 2013 (IT) .............................. MI2013A0553

(51) Int. Cl.
| | |
|---|---|
| C07C 213/00 | (2006.01) |
| C07C 315/02 | (2006.01) |
| C07C 317/14 | (2006.01) |
| C07C 317/36 | (2006.01) |
| C07C 323/09 | (2006.01) |
| C07C 319/18 | (2006.01) |

(52) U.S. Cl.
CPC ............. *C07C 315/02* (2013.01); *C07C 317/14* (2013.01); *C07C 317/36* (2013.01); *C07C 319/18* (2013.01); *C07C 323/09* (2013.01)

(58) Field of Classification Search
None
See application file for complete search history.

(56) References Cited

U.S. PATENT DOCUMENTS

| 2,385,899 A | 10/1945 | Weijiard |
| 2008/0293970 A1 | 11/2008 | Villa et al. |

FOREIGN PATENT DOCUMENTS

| EP | 0102476 A1 | 3/1984 |
| WO | WO 2011142381 A1 * | 11/2011 |

OTHER PUBLICATIONS

Clark, J H et. al., "Fluorodenitration of activated diphenyl sulphones using tetramethylammonium fluoride," Journal of Fluorine Chemistry, Elsevier, NL, vol. 70, No. 2, Feb. 1, 1995 (Feb. 1, 1995), pp. 201-205.
Fromm, E et al., "Derivate desp-Nitrothiophenols," Berichte Der Deutschen Chemischen Gesellschaft, vol. 41, No. 2, May 1908 (May 1, 1908), pp. 2264-2273.
Huang, Xian et al., "Synthesis of Bisalkylthiolydine Derivatives of Meldrum's Acid and Barbituric Acid," Synthesis, vol. 1986, No. 11, Jan. 1, 1986, pp. 967-968.
Italian Search Report issued in Application No. MI20130553, dated Jul. 15, 2013, 35 pages.
Price, Charles C et al, Journal of the American Chemical Society, vol. 68, No. 3, Mar. 19, 1946, pp. 498-500.
Sanghavi, N.M., "Dapsone," Indian Chemical Journal, Jul. 1971, 6(1), pp. 179-181.
Smith, F.E. et al. "Notes," Journal of the Chemical Society (Resumed), Jan. 1, 1946, p. 542.
Stec, Z et al., "Oxidation of sulfides with H2O2 catalyzed by Na2WO4 under phase-transfer conditions," Polish Journal of Chemistry, Polskie Towarzystwo Chemiczne, PL, vol. 70, Jan. 1, 1996 (Jan. 1, 1996), pp. 1121-1123.

* cited by examiner

*Primary Examiner* — Sudhakar Katakam
(74) *Attorney, Agent, or Firm* — Rothwell, Figg, Ernst & Manbeck, P.C.

(57) ABSTRACT

Process for the preparation of known sulfonamides having antibacterial activity applicable on industrial scale, which allows their production in high yields and purity, comprising in particular the step of nucleophile aromatic substitution and oxidation in suitable conditions.

14 Claims, 1 Drawing Sheet

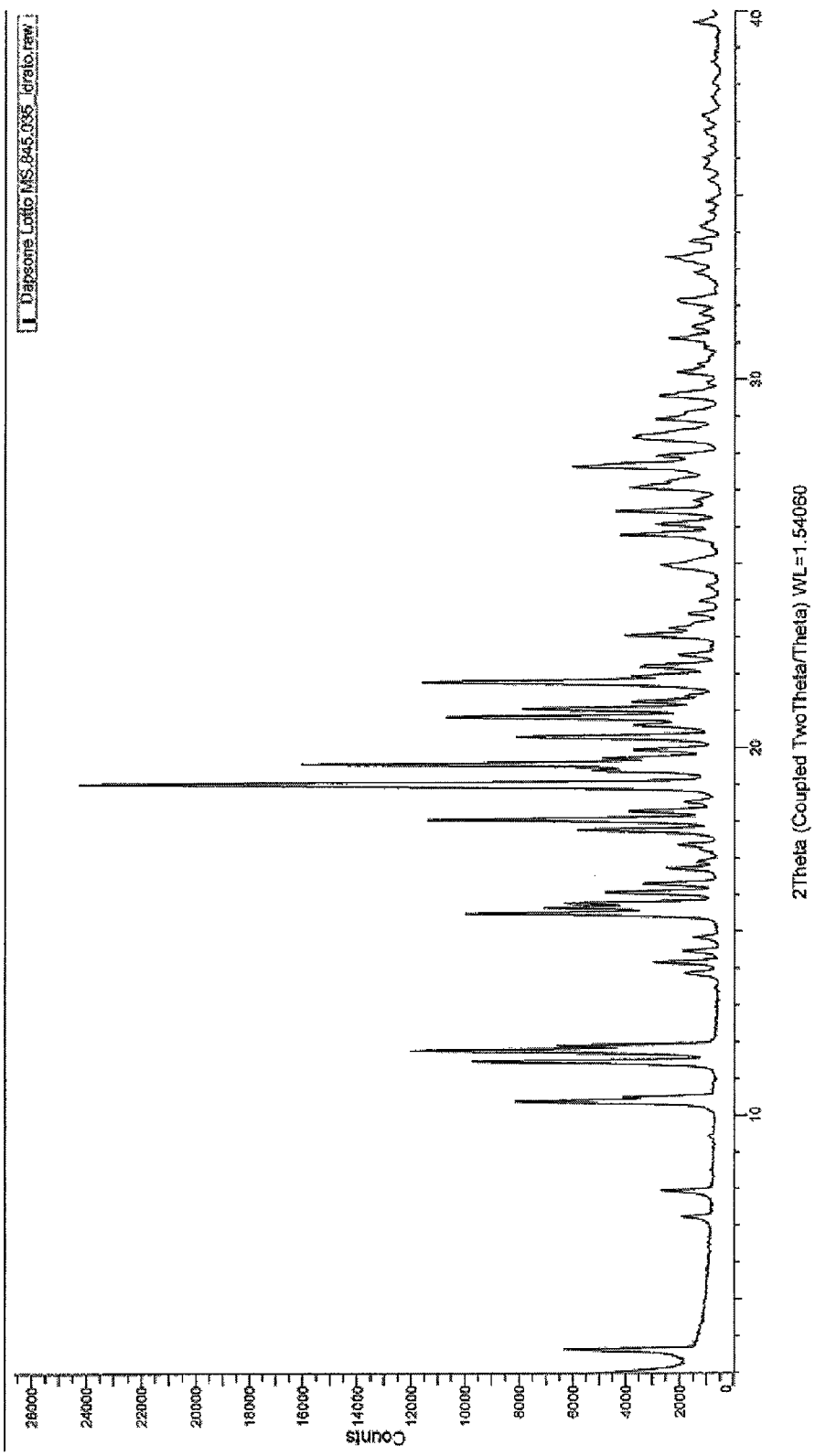

PROCESS FOR THE PREPARATION OF SULFONAMIDE COMPOUNDS

TECHNICAL FIELD

The present invention relates to a process for the preparation of 4-4'-dinitrophenyl-sulfide and its use in preparing 4-4'-diamino-diphenylsulfone, also known as Dapsone, having known antibacterial activity.

BACKGROUND ART 4-4'-Diamino-diphenylsulfone has been used for a long time in therapy as an antibacterial and in the treatment of dermatologic diseases.

In particular, it is used in clinical medicine, in association with rifampin and clofazimine, in the treatment of the leprosy.

The preparation of Dapsone is known for a long time and the synthetic methods for its preparation are interesting.

Indian Chemical Journal: 1971, 6(1), 179-181 discloses several methods. One of them, for example, teaches the preparation by a process which comprises the reaction between $Na_2S$ and p-chloronitrobenzene to obtain p-nitrothiophenol that by reaction with another equivalent of p-chloronitrobenzene forms the diamino-compound. This is acetylated by treatment with acetic acid/acetic anhydride at reflux to form the diacetylamino-compound, which is then oxidized with dichromate in glacial acetic acid. The so obtained 4,4'-diacetylaminodiphenyl sulfone is then hydrolyzed to obtain Dapsone.

Another method comprises the use of a substrate 4,4'-dinitrophenyl sulfide; the oxidation is then carried out for example with peroxides or permanganate. U.S. Pat. No. 2,385,899 discloses the oxidation of 4,4'-dinitro-diphenyl sulfide and 4,4'-diacetylaminodiphenyl-sulfide with sodium hypochloride in acetic acid at 85° C. EP 102 476 discloses the oxidation of the sulphinyl substrate to sulphone by treatment with 30% $H_2O_2$ in glacial acetic acid, as solvent, at about 100° C.

Notwithstanding several synthetic methods for preparing Dapsone have been used for a long time, it is well known that various by-products and impurities can form during its preparation and their removal requires troublesome operations, scarcely compatible with its production on industrial scale.

The object of the present invention is to provide a new synthetic process for preparing Dapsone, more suitable for its preparation on industrial scale, improving the yield and the purity, and, at the same time, also reduces the costs and is environmentally friendly.

BRIEF DESCRIPTION OF THE FIGURE AND ANALYTICAL METHODS

The X ray diffraction spectra (XRPD) for 4-4'-diamino-diphenylsulfone (Dapsone), of formula (IV) in crystalline form, herein defined Form A, have been recovered with an automatic powder diffractometer D8 Advance Bruker in the following operating conditions: Bragg-Brentano geometry, radiation CuKa ($\lambda$=1.54 Å), scansion with angular range 3-40° in 2θ, angular step 0.02° for a time of 0.5 sec. The detector used is LynxEye.

The melting point has been obtained by using a capillary tube with a velocity of 10° C./min.

The content of water of 4-4'-diamino-diphenylsulfone in crystalline form, herein defined as Form A, has been determined by titration with Karl Fisher technique.

FIGURE: Spectrum XRPD of 4-4'-diamino-diphenylsulfone in anhydrous crystalline form, herein defined as Form A, wherein the main peaks (expressed in ° in 2θ) fall at: 10.39; 11.47; 11.77; 15.48; 18.04; 19.00; 19.56; 20.29; 20.83; and 21.79±0.2° in 2θ.

SUMMARY OF THE INVENTION

The invention relates to a process for the preparation of 4-4'-dinitrophenyl-solfide and the use in the preparation of 4,4'-diamino-diphenylsulfone.

DETAILED DESCRIPTION OF THE INVENTION

The invention provides, as a first object, a process for preparing a compound of formula (I)

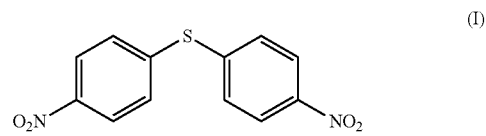 [SMILES: O=[N+]([O-])c1ccc(Sc2ccc([N+](=O)[O-])cc2)cc1]
(I)

comprising reacting a compound of formula (II)

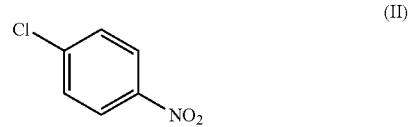
(II)

with a compound of formula (III)

(III)

wherein R is a $C_1$-$C_6$ alkyl or a phenyl group, in presence of a base and in a solvent.

A $C_1$-$C_6$ alkyl group, which can be straight or branched, is for example a $C_1$-$C_4$ alkyl group, in particular methyl, ethyl, propyl, isopropyl and butyl, preferably methyl.

A base can be for example an inorganic base, preferably a strong base, selected from the group comprising sodium hydroxide, potassium hydroxide, sodium carbonate and potassium carbonate, preferably potassium carbonate.

A solvent is for example water or a mixture thereof with one or more solvents, preferably one or two, miscible with water and selected for example from tetrahydrofuran, dioxane and a $C_1$-$C_6$ alkanol, preferably a $C_1$-$C_4$ alkanol, for example methanol, ethanol and isopropanol, preferably isopropanol. A solvent is preferably a water/isopropanol mixture.

The reaction can be for example carried out at reflux temperature of the reaction mixture for a time comprised between about 8 and about 16 hours, typically between about 12 and about 14 hours.

As it can be appreciated from the experimental part, the new process provides a compound having formula (I) with a high yield and purity.

A so obtained compound of formula (I), can be used as starting material in a process for preparing 4-4'-diamino-diphenylsulfone (Dapsone) having formula (IV)

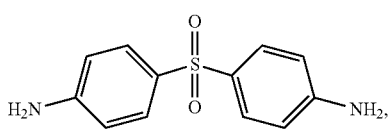

(IV)

for example, in a process comprising:
the oxidation of a compound of formula (I) to obtain a compound of formula (V); and

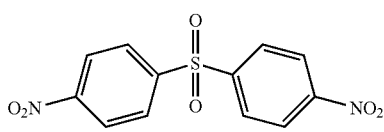

(V)

the reduction of a compound of formula (V) to obtain 4-4'-diamino-diphenylsulfone of formula (IV).

Oxidation of a compound of formula (I) is preferably carried out by a process comprising the treatment with hydrogen peroxide in the presence of a tungstate salt and an acid.

The hydrogen peroxide used as oxidizing agent can be a 30-35% aqueous solution thereof, preferably a 30% aqueous solution.

The amount of hydrogen peroxide that can be used in the reaction is typically comprised between about 2.0 and about 4.35 equivalents, preferably between about 2.0 and about 2.5 equivalents to the substrate, more preferably between about 2.1 and about 2.2 equivalents.

According to the invention, a tungstate salt, used as catalyst in the oxidation process, is typically sodium tungstate dihydrate.

The amount of sodium tungstate that can be used in the reaction is typically comprised between about 0.5% and about 0.05% molar, preferably about 0.1 molar.

According to the oxidation process of the invention, the acid, whose use is typically as reaction promoter, can be a mineral acid, for example, selected from hydrochloric acid, sulfuric acid, phosphoric acid; or an organic acid, for example, selected among acetic acid, methanesulfonic acid and a phosphonic acid, in particular phenylphosphonic acid. Preferably the acid is glacial acetic acid.

The reaction can be carried out in a monophasic or biphasic system.

Preferably, acetic acid, typically glacial acetic acid, can be used in a monophasic system as acid reaction promoter.

In a biphasic system, preferably phenylphosphonic acid can be used as acid reaction promoter, preferably in a substantially equimolar amount to the catalyst.

The reaction can be carried out in a range of pH comprised between about 1 and about 6, preferably between about 1 and about 2.

In a monophasic system the solvent can be for example an excess of acetic acid or a solvent selected among a straight $C_1$-$C_6$ alkanol, in particular methanol or ethanol, water, tetrahydrofuran and dioxane, or a mixture typically of two of them. In a monophasic system the solvent is preferably glacial acetic acid.

In a biphasic system the solvent can be for example a solvent selected among a chlorinated solvent, typically dichloromethane, trichloromethane, tetrachloromethane, trichloroethane, tetrachloroethane, in particular dichloromethane, and a $C_1$-$C_4$ alkyl ester of a carboxylic acid, typically ethyl acetate.

When the reaction is carried out in a biphasic system, a phase transfer can also be advantageously used, for example selected from tetrabutylammonium hydrogensulfate, butylammonium chloride, tetrabutylammonium hydroxide, tetramethylammonium chloride, benzyltrimethylammonium chloride, methyltrioctylammonium chloride, aliquat 175 (methyltributylammonium chloride), dodecyltrimethylammonium chloride and dimethyldioctadodecylammonium chloride, preferably tetrabutylammonium hydrogensulfate.

The reaction can be carried out at a temperature comprised between about 60 and about 98° C., preferably between about 85 and about 95° C., more preferably between about 90 and about 95° C.

According to a preferred aspect of the invention, the oxidation reaction can be carried out in a monophasic system, using as oxidizing agent 30% hydrogen peroxide in glacial acetic acid, at a pH lower than 2, sodium tungstate dehydrate in an amount of about 0.1 molar, at a temperature comprised between about 90 and about 95° C.

The reduction of a compound of formula (V) to obtain a compound of formula (I) can be carried out according to known methods, for example as reported in Indian Chemical Journal: 1971, 6(1), 179-181.

According to a preferred embodiment, the reduction of a compound of formula (V) can be carried out by hydrogenation in the presence of a platinum (Pt) or palladium (Pd) based catalyst, typically Pt/C or Pd/C, preferably 5% Pd on 50% wet carbon, in an aqueous solution of methanesulfonic acid, under hydrogen pressure at about 4-5 atm., and at a temperature of about 55-60° C., in a time of about 8 hours.

An end-reaction crude of the preparation of a compound of formula (IV), 4-4'-diamino-diphenylsulfone (Dapsone), can then be submitted to a purification process by crystallization from a mixture of isopropanol and water to obtain dry Dapsone in a crystalline form, as herein defined Form A. Such form has a chemical purity evaluated by HPLC greater than or equal to 98.5%, preferably greater than or equal to 99%.

A further object of the invention is Dapsone in crystalline form A, as herein defined, having a melting point of 178.8° C. and a XRPD spectrum as illustrated in FIGURE, wherein the most intense peaks fall at 10.39; 11.47; 11.77; 15.48; 18.04; 19.00; 19.56; 20.29; 20.83; and 21.79±0.2° in 2θ. The water content in such crystalline form, determined by Karl Fisher titration results of about 0.8%, so as to be defined as crystalline anhydrous form.

The particle size of the crystals of a so obtained compound of formula (IV), that is dry Dapsone in crystalline anhydrous form A, is characterized by a $D_{50}$ value comprised between about 25 and 250 μm. If desired, such value can be reduced by micronization or fine grinding.

The following examples illustrate the invention.

Example 1

Synthesis of 4,4'-dinitrodiphenylsulfide

In a flask under nitrogen atmosphere 4-nitrothiophenol (0.156 mol, 25.0 g), 4-nitrochlorobenzene (0.156 mol, 24.9 g), potassium carbonate (0.172 mol, 23.8 g), water (200 ml) and isopropanol (165 ml) are loaded. The so obtained mixture is heated at reflux temperature (80-82° C.) for 8 hours. The mixture is cooled to room temperature and the product is filtered off by washing the solid with a solution of water/isopropanol 2:1 (40 ml for three times). The product is dried in oven under vacuum and at 50° C. for one night. 41.0 g of 4,4'-dinitrodiphenylsulfide are obtained with a yield of 95%. m.p.: 159° C.; H$^1$-NMR (CDCl$_3$) δ8.20 (4H, d); 7.50 (4H, d).

Example 2

Synthesis of 4,4'-dinitrodiphenylsulfide

In a flask under inert atmosphere 4-nitrochlorobenzene (50.0 g, 0.317 mol), potassium carbonate (48.2 g, 0.349 mol), water (200 ml) and isopropanol (162 ml) are loaded at room temperature. Thioacetic acid (13.3 g, 0.174 mol) is then dropped in (13.3 g, 0.174 mol) in about 30 minutes and the mixture is heated at reflux temperature for 12-14 hours. The mixture is then left to slowly cool to room temperature and the solid is filtered off, washing the solid with a mixture of water/isopropanol 2:1 (50 ml for three times). After drying for a night in an oven at 50° C. under vacuum 40.4 g of 4,4'-dinitrodiphenylsulfide are obtained with a yield of 92%. m.p.: 159° C.; purity HPLC: 95%; H$^1$-NMR (CDCl$_3$) δ8.20 (4H, d); 7.50 (4H, d).

Example 3

Synthesis of 4,4'-dinitrodiphenylsulfone

In a flask at room temperature 4,4'-dinitrodiphenylsulfide (0.148 mol, 41.0 g) is suspended in glacial acetic acid (205 ml); a solution of sodium tungstate dihydrate (0.0015 mol, 0.50 g) in water (1.7 ml) is added, and the mixture is heated at a temperature of 75-80° C. A solution of 30% hydrogen peroxide (0.311 mol, 35.3 g) is slowly dropped in about 1.5 hours, and the temperature let to rise till 90-95° C. After the addition is completed, the mixture is left to react for 2.5-3 hours at 75-80° C. The mixture is cooled to room temperature and the solid is filtered washing abundantly with water (100 ml for three times). The solid is dried in oven under vacuum at a temperature of 50° C. for a night, obtaining 41.6 g of crude product. The solid is suspended in methylisobutylketone (400 ml) and heated at reflux temperature for about 2 hours, then cooled to room temperature and filtered off. After drying in oven at 50° C. 39.9 g 4,4'-dinitrodiphenylsulfone are obtained with a total yield of 87%. m.p.: 256° C.; purity HPLC: 98%.

Example 4

Synthesis of 4,4'-diaminodifenilsolfoxide (Dapsone)

In autoclave at room temperature 4,4'-dinitrodiphenylsulfone (0.0649 mol, 20.0 g), 5% palladium on 50% wet carbon (1.4 g), 70% methanesulfonic acid in water (0.130 mol, 17.8 g), water (10 ml) and methanol (70 ml) are loaded. The mixture is left to react under hydrogen pressure (4-5 atm) at a temperature of 55-60° C. for about 8 hours. The mixture is filtered on a Perlite layer washing with methanol (10 ml for 2 times), subsequently with water (80 ml). The solution is concentrated under reduced volume to remove the organic phase. The aqueous phase is extracted with ethyl acetate (50 ml for 3 times) and the organic washings are discarded. Discolouring carbon (1.0 g) is added under vigorous stirring and after 15-20 minutes the mixture is filtered on a Perlite layer. To the aqueous solution heated at about 50° C. a aqueous solution of 30% sodium hydroxide is slowly added to reach a pH higher than 10. After about 30 minutes the mixture is cooled to 0-5° C. and then filtered, washing the solid with water cooled at 0-5° C. (20 ml for three times). After oven-drying at 50° C., 11.2 g of crude Dapsone are obtained that are then crystallized from a mixture of isopropanol (35 ml) and water (25 ml) to obtain 10.2 g of dry Dapsone, having a chemical purity evaluated by HPLC equal to about 98.5%.

The so obtained crystalline product, herein defined Form A, with m.p. 178.8° C., shows a XRPD spectrum as illustrated in FIGURE, wherein the most intense peaks fall at 10.39; 11.47; 11.77; 15.48; 18.04; 19.00; 19.56; 20.29; 20.83; and 21.79±0.2° in 2θ. The water content in the compound, determined by Karl Fisher titration, resulted of about 0.8%, so as to be defined as a anhydrous crystalline form.

The invention claimed is:

1. A process for preparing a compound of formula (I)

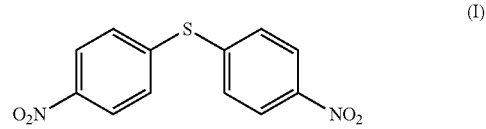 [SMILES: O=[N+]([O-])c1ccc(Sc2ccc([N+](=O)[O-])cc2)cc1]

(I)

comprising reacting a compound of formula (II)

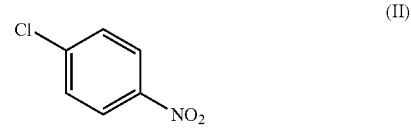

(II)

with a compound of formula (III)

(III)

wherein R is a C$_1$-C$_6$ alkyl group or phenyl group,
in the presence of a base and in a solvent.

2. The process according to claim 1, wherein the base is an inorganic base selected from the group consisting of sodium hydroxide, potassium hydroxide, sodium carbonate and potassium carbonate.

3. The process according to claim 1, wherein the base is potassium carbonate.

4. The process according to claim 1, wherein the solvent is water or a mixture of water and one or more solvents miscible with water.

5. The process according to claim 1, wherein the solvent is a water/isopropanol mixture.

6. A process for preparing 4-4'-diamino-diphenylsulphone (Dapsone) having formula (IV)

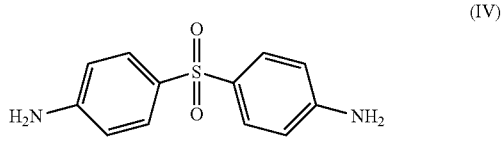

(IV)

comprising:
reacting a compound of formula (II)

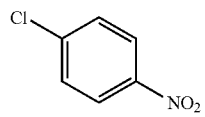

with a compound of formula (III)

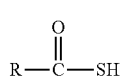

wherein R is a $C_1$-$C_6$ alkyl group or phenyl group;
in the presence of a base and in a solvent to obtain a compound of formula (I)

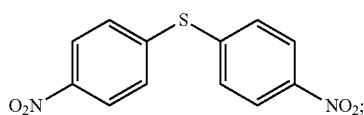

oxidizing a compound of formula (I) with hydrogen peroxide in presence of a tungstate salt and of an acid to obtain a compound of formula (V)

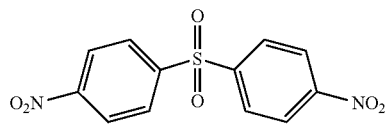

reducing the compound of formula (V) to obtain 4-4'-Diamino-diphenylsulphone (Dapsone); and optionally, crystallizing Dapsone to obtain Dapsone as crystalline anhydrous form A, having XRPD spectrum as illustrated in FIG. 1, wherein the most intense peaks fall at 10.39; 11.47; 11.77; 15.48; 18.04; 19.00; 19.56; 20.29; 20.83; and 21.79±0.2° in 2θ.

7. The process according to claim 6, wherein hydrogen peroxide is a 30-35% aqueous solution.

8. The process according to claim 6, wherein the tungstate salt is sodium tungstate dihydrate of about 0.5% to about 0.05% molar.

9. The process according to claim 6, wherein the acid is a mineral acid selected from the group consisting of hydrochloric acid, sulfuric acid and phosphoric acid;
or an organic acid selected from the group consisting of acetic acid, methanesulphonic acid and a phosphonic acid; and
the reaction is carried out at a pH ranging from about 1 and about 6.

10. The process according to claim 6, wherein the oxidizing step is carried out in a monophasic system,
with 30% hydrogen peroxide in-glacial acetic acid,
at a pH lower than 2,
with sodium tungstate dihydrate in an amount of about 0.1 molar, and
at a temperature comprised between about 90 and about 95° C.

11. A process for preparing 4-4'-diamino-diphenylsulphone (Dapsone) having formula (IV)

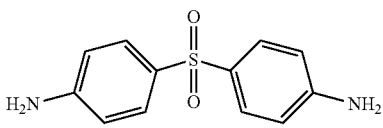

comprising:
reacting a compound of formula (II)

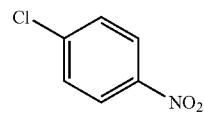

with a compound of formula (III)

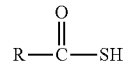

wherein R is a $C_1$-$C_6$ alkyl group or phenyl group;
in the presence of a base and in a solvent to obtain a compound of formula (I)

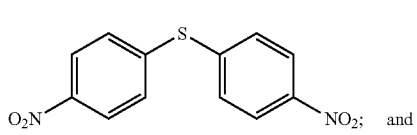

subsequently converting a compound of formula (I) to a compound of formula (IV).

12. The process according to claim 1, wherein said solvent miscible with water is tetrahydrofuran, dioxane or a $C_1$-$C_6$ alkanol.

13. The process according to claim 6, wherein the acid is phenylphosphinic acid.

14. The process according to claim 7, wherein the hydrogen peroxide is used in an amount between about 2.0 and about 4.35.

* * * * *